United States Patent
Chang et al.

(10) Patent No.: US 7,895,938 B2
(45) Date of Patent: Mar. 1, 2011

(54) APPARATUS AND METHOD FOR STEAM DISINFECTION OF LIQUID DISPENSING MACHINE

(76) Inventors: Chung Chang, Wilton, CT (US); Tung-Sheng Chang, Cupertino, CA (US); Alexander Chang, Wilton, CT (US); Chung-Hsing Chris Lee, Cupertino, CA (US); Jean Saint Germain, Ridgefield, CT (US)

( * ) Notice: Subject to any disclaimer, the term of this patent is extended or adjusted under 35 U.S.C. 154(b) by 1108 days.

(21) Appl. No.: 11/163,385

(22) Filed: Oct. 17, 2005

(65) Prior Publication Data
US 2007/0084351 A1    Apr. 19, 2007

(51) Int. Cl.
A47J 31/44    (2006.01)
A23B 5/005    (2006.01)
E21B 7/15    (2006.01)

(52) U.S. Cl. .......................... 99/293; 426/399; 392/303
(58) Field of Classification Search .................. 99/279, 99/280, 281, 282, 283, 284, 285, 286, 287, 99/288, 289, 290, 291, 292, 293; 222/185.1–189.11; 422/11, 26, 284; 426/399; 392/303, 386–406
See application file for complete search history.

(56) References Cited

U.S. PATENT DOCUMENTS

| | | | |
|---|---|---|---|
| 6,123,232 A | 9/2000 | Donselman | 222/185.1 |
| 6,207,046 B1 * | 3/2001 | Yamashita et al. | 210/138 |
| 6,220,311 B1 * | 4/2001 | Litto | 141/67 |
| 7,316,249 B2 * | 1/2008 | Cheong | 141/100 |
| 2003/0188769 A1 * | 10/2003 | Eisenberg et al. | 134/57 D |
| 2005/0006405 A1 | 1/2005 | Tang | 222/146.6 |
| 2005/0087554 A1 | 4/2005 | Shelton | 222/189.06 |
| 2007/0084351 A1 * | 4/2007 | Chang et al. | 99/275 |

* cited by examiner

*Primary Examiner* — Daniel L Robinson

(57) ABSTRACT

A method and apparatus using steam to sterilize liquid dispensers. This is achieved by injecting steam into a drained dispenser machine equipped with a cover having a safety valve that matches the top of the dispenser to provide sealing. The steam is generated by a steam generator physically integrated with the new liquid dispenser machine. The steam circulates through the fluid compartment of the liquid dispenser and continues through its conduits and exits at the taps which are held open by a stepped boss. The sanitizing period can be adjusted and controlled. After sterilizing the machine, the cap of the dispenser is removed and its taps are released in order to return the machine back to its normal operation.

13 Claims, 6 Drawing Sheets

APPARATUS AND METHOD FOR STEAM DISINFECTION OF LIQUID DISPENSING MACHINE

FIELD OF INVENTION

The present invention relates generally to sanitizing beverage dispensers, such as refrigerated water, beverage coolers, beverage brewing system or hot beverage dispenser. More particularly, the present invention is directed to bottled type water dispenser.

DESCRIPTION OF THE RELATED ART AND BACKGROUND INFORMATION

Due to increasing environmental pollutions of water resources more people are relying on water dispensers at home and work places to provide drinking water. Sale of water dispensers has increased rapidly. Water dispensers are well known in the art for containing a supply of purified water and commonly include an upwardly open water reservoir mounted within a cooler housing or cabinet adapted to receive and support an inverted water bottle of typically three to five gallon capacity. The water within the bottle flows downward into the water reservoir, and depending upon the design, one or more taps dispense water to the user.

Although bottled water is cleaned and purified by the water bottle company, often the water dispenser is operated for months without proper disinfection maintenance. Bacteria in air can get into the dispenser machine and grow inside. Usually there are recommended instructions for cleaning the water dispenser to disinfect it periodically. However, the cleaning process is time consuming and may involve taking apart the system with special tools and may sometimes require chemical(s) in order to kill the microbial. Rinses are often required to get rid of such chemical residue and the smell introduced during the cleaning process. Due to the above reasons, most users tend to neglect these recommended cleanings until serious health problem occurs.

Inherent in the current water dispenser design are problems associated with sterility. To address the sanitizing problem, a liquid dispenser with a better hygienic adapter that is easier to take apart has been invented as described by U.S. Pat. No. 6,123,232. However, that invention does not address the many hard to reach internal surfaces associated with the plumbing of the dispenser machine, where bacteria can reside. U.S. Pat. No. 20050087554A1 describes a method and apparatus for disinfecting a refrigerated water cooler reservoir by generating ozone for sanitizing the water. However, since the bottle water has already been processed with ozone, repeating the same process inside a water dispenser for the purpose of sanitizing the machine is not economical. Furthermore, it is the machine that needs to be sterilized not the water. It is better to have a sterilizing system that is simple, effective and economical. PCT publication WO 01/52909 A1 describes a method and device for sanitizing bottled water dispensers using an external steam generator. However, there is a wide variety of water dispensers each with a different internal design; a typical modern dispenser with hygienic design often prevents the user from seeing the water remaining inside the water reservoir. A direct injection of steam without knowledge about the water left inside the dispenser machine may cause serious injury. Another potential problem that has not been considered by patent application WO 01/52909 A1 is that an advanced water dispenser machine using electric valves to dispense water cannot be turned off while disinfecting the machine. The refrigeration thus can turn on automatically upon introducing hot steam into the machine, directly interfering with the disinfection process. In addition the sterilization would not be thorough due to many internal surfaces and pockets still covered by residual water, as well as cold spots due to refrigeration; the external device is not only cumbersome, but also not economical and not suitable for performing a complete and safe disinfection process. Furthermore, the methods described by patent application WO 01/52909 A1 omitted the critical step of emptying the remaining water in the system before introducing the pressurized steam into the flow path. Its methods, therefore, are not sufficient to ensure a safe operation.

Considering the users may consist of a wide spectrum of age and intelligence, a better and safer water dispenser with disinfection capability is needed. In other words, a modern water dispenser machine should include sensors that indicate the readiness of the machine for performing the sterilization procedure, as well as monitoring the completeness of the process. In addition, the present invention installs a mechanical safety valve on the sealing cover to prevent accident due to a malfunction of the water dispenser machine and its sterilization.

Hot steam is also widely used in commercial products. It is technologically feasible to integrate a steam generator with a water dispenser machine. In fact, it is better and safer to invent a new water dispenser machine appropriate for steam sterilization rather than trying to adapt this new technology to existing water dispensers that are not designed for steam disinfection. However, it is challenging to invent a water dispenser machine having steam sterilization capability, without significantly altering its original designs and functions in order to keep the production cost at its minimum. An invention that includes this new health improvement technology, yet still providing customers with an easy and safer operation and leaving them with the various choices of different water dispenser, is essential to the market.

SUMMARY OF THE INVENTION

In order to solve this worldwide hygienic problem, an object of the present invention is to incorporate a steam sterilizing function into the water dispenser machine, which can sterilize the system by itself. Disinfection can be accomplished without taking the dispenser apart and without chemical additives. Currently there are no such water dispenser machines available.

Other objects and further scope of applicability of the present invention will become apparent from the detailed description given hereinafter. It should be understood, however, that detailed description and specific examples, while indicating the preferred embodiments of the invention, are given by way of illustration only, since various changes and modifications within the spirit and scope of the invention will become apparent to those skilled in the art from the detailed description.

To achieve this object, pursuant to an embodiment of the present invention, a steam generating module is physically combined with a liquid dispenser machine preferably inside the cabinet for safety reason. The steam generator of the present application includes a boiler, a water container, a steam discharge switch and optionally a pump. The water container is preferably detachable from the steam generator to facilitate easy refilling thereof. After the water bottle is removed and the cooling function of the dispenser stopped, one can proceed to drain the remaining water out of the dispenser machine, and lock down both handles of the taps in an open position by a simple stepped boss to allow them to serve as steam discharging ports. Installing sensors that can detect residual water in the reservoir, as well as the temperatures at the cold spots of the flow path can enhance the safety of the operation and the completeness of the disinfection. A threaded cover lid with a pressure relief valve for preventing excessive pressure in the system can be screwed onto the bottle supporting seat to prevent steam from escaping at the top of the dispenser. Preferably hot steam is injected into the reservoir container at orifices around the ring of the bottle supporting seat. Injecting steam via the seat requires a minimal modification to water dispenser machines produced by many different manufactures. Steam injection can also be located at other suitable places along the flow path. The steam will then circulate through the flow path and exit at the taps of the dispenser. Although it is known in the prior art that sterilization temperature above 63° C. is sufficient, we prefer to use hotter dry steam with temperature between 100° C. to 160° C. for an extended period of time, depending on the size and the temperature inside the water dispenser due to likely residual water left in the system and possible cold spots along the flow path. For example, 10 minutes can be chosen on an adjustable timer as the desired disinfection period to kill the bacteria in the system. Hotter steam i.e. 160° C. will reduce the time required for the disinfection. However, the steam temperature will have to be compatible with the temperature rating of the materials used in constructing the flow path(s) of the dispenser. Preferably a controller that can vary the temperature and pressure of the output steam and a timer that can control the time duration of the steam disinfection are jointly incorporated to facilitate with the sanitization. After disinfecting the water dispenser, the handles of the taps can then be released, and a new bottle of water can be put on the dispenser for the regular usage of the machine. For a dispenser using electrical control valves, those valves will have to be open when necessary to allow for discharging of the hot steam while disinfecting the system.

BRIEF DESCRIPTIONS OF THE FIGURES

DESCRIPTION OF THE PREFERRED EMBODIMENTS

Figure 1:
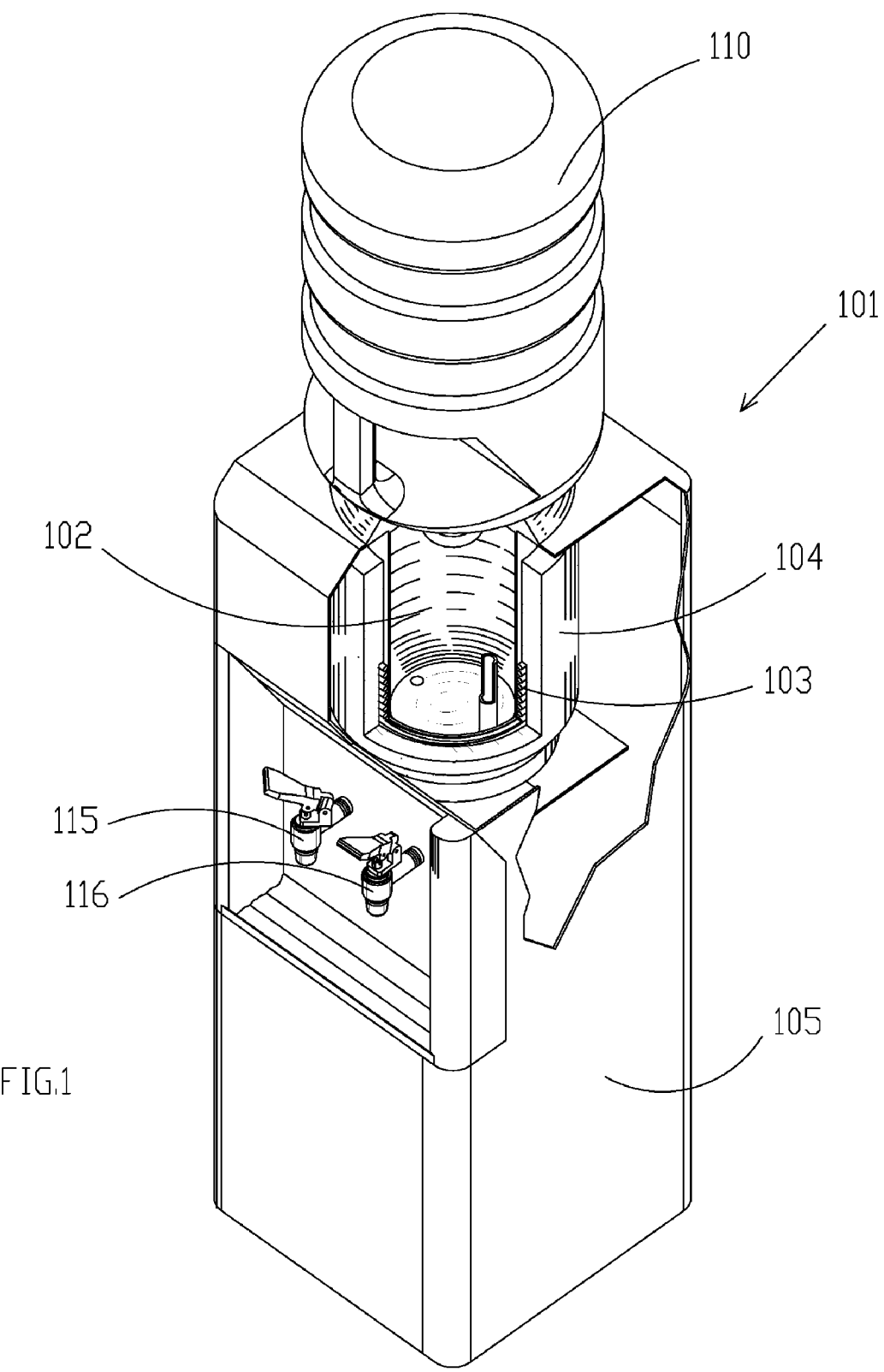
FIG. 1 is a perspective and partial cutaway view of a typical water dispenser.

Referring to the figures and, in particular, FIG. 1 shows a typical water dispenser 101, having a water reservoir 102, a cooling coil 103, thermo shielding material 104 and a body 105 that can receive an inverted water bottle 110 on top, and dispense water through two taps 115 and 116.

Figure 2:
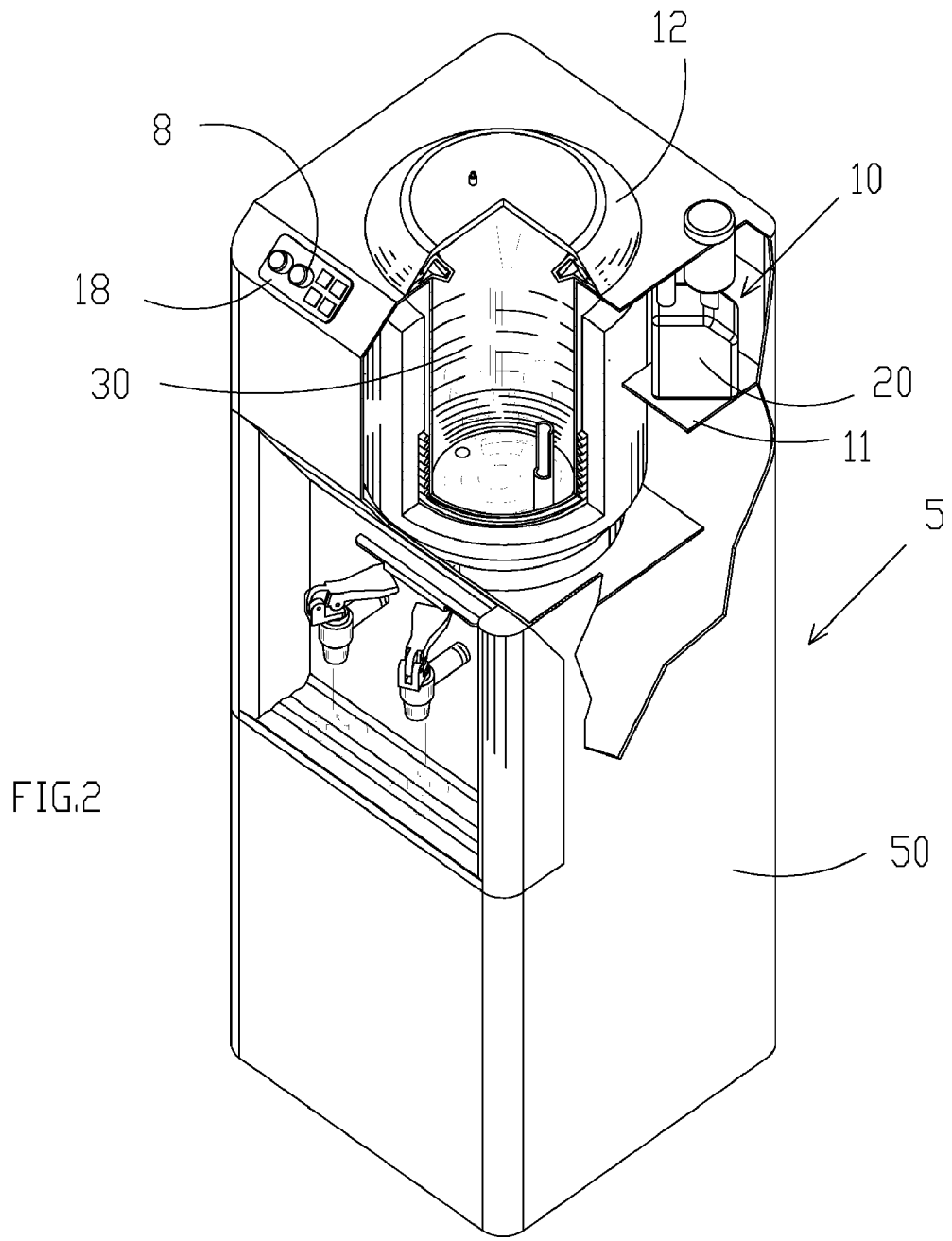
FIG. 2 is a perspective and a partial cutaway view of the present invention that incorporates a steam generator for disinfecting the system.

FIG. 2 shows the preferred embodiment of water dispenser 5 of the present invention that includes a steam generator 10, its mounting plate 11 and a cover 12 that can be seen in the sectional cutaway view in addition to traditional water dispenser components shown in FIG. 1. The steam generator 10 has a housing 50 that houses and encloses a boiler 20. Dial switch 18 is to activate and control the period of steam generation and dial switch 8 is to select a particular steam temperature.

Figure 3:
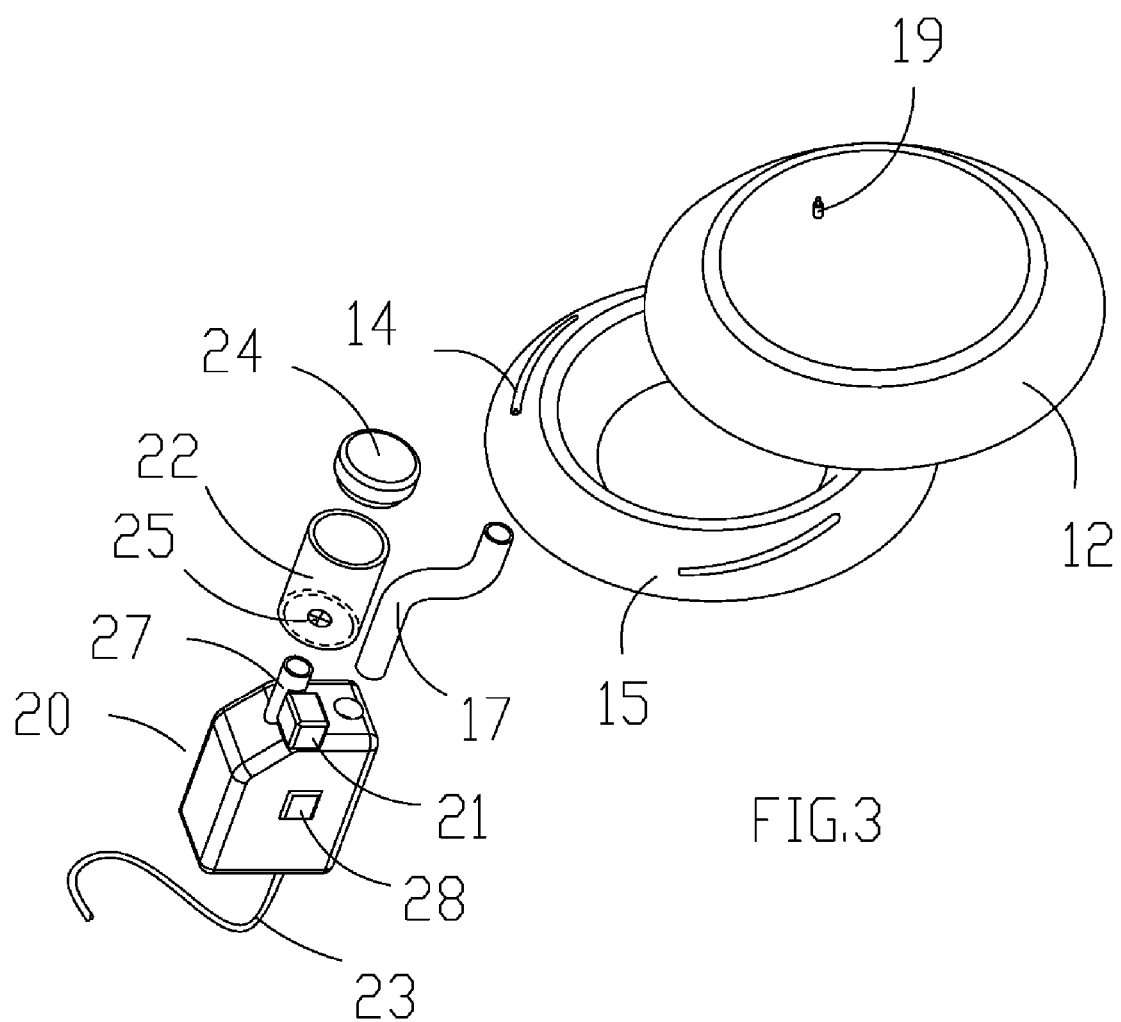
FIG. 3 is an exploded view of the steam generator of the present invention.
Figure 4:
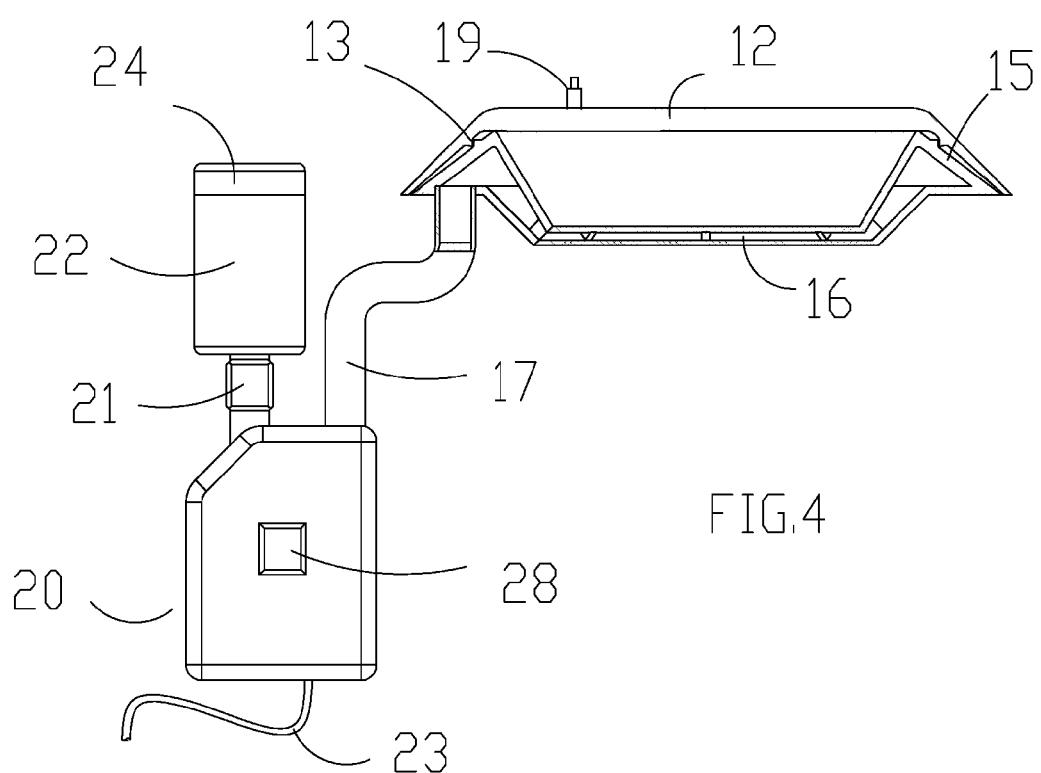
FIG. 4 is a sectional view of the cover and the seat of the preferred water dispenser.

As shown in FIG. 3-4, steam generator 10 includes boiler 20, a flow control device 21 and a water tank 22, as well as a power cable 23. Power cable 23 provides an electrical connection from the external power source of the dispenser to boiler 20, the flow control device 21 and other components of the steam generator 10 requiring electrical energy. The steam generator is activated through the steam generator dial switch 18 of FIG. 2. The flow control device 21 can be a pump, electronic valve(s) or a combination of a pump and electric valve(s). Pressure relief valve 19 prevents excessive pressure inside the system due to potential operational mistakes.

Water tank 22 is preferably detachable from housing 50, and is to be filled with water through cap 24. Water tank 22 includes a valve 25 to prevent spillage while water tank 22 is disengaged from housing 50. Once filled, water tank 22 can be connected to housing 50 so that a water conducting pipe 27 engages with valve 25 to conduct water. Through pipe 27, flow control device 21 is in fluid communication with water tank 22 and boiler 20.

Upon activation, the steam generator dial switch 18 connects electrical power to activate the steam generator 10. The steam generator dial switch 18 serves also as a timer to control the duration of the disinfection period. The flow control device 21 pumps water from water tank 22 through pipe 27 to boiler 20. Boiler 20 preferably is a flash boiler that can produce steam practically instantaneously upon receiving water from the pump. In order to control the production of steam by boiler 20, the amount and flow rate of water delivered to boiler 20 and the heating capacity of the boiler will have to be compatible in order to sustain continuous steam generation. Preferably, the amount and flow rate of water delivered to boiler 20 and the heating capacity of boiler 20 are controlled by a thermostatic control device 28 capable of delivering a controllable steam output volume for a long period of time at substantial pressure. Thermostatic control device 28 can also provide thermal cut-off to prevent overheating of boiler 20. Thermostatic control device 28 may be connected to dial switch 8 of FIG. 2 to control the temperature of the steam.

The cover 12 of the water dispenser 5 has a thread 13 which mates with thread 14 on the bottle supporting seat 15 to provide a seal for the steam. A conventional bottle type water dispenser has a seat generally an annular ring structure built around the water inlet to support the shoulder portion of an inverted bottle and its weight. Cover 12 also confines the space that needs to be disinfected and allows for a higher efficiency. It should be appreciated that the particular type of cover seal used may vary and can include any other types of cover seal mechanical designs or even use a capped and filled water bottle. The benefit of using a capped and filled water bottle to provide seal is that one can also disinfect the surface area around its cap. Steam conducting pipe 17 connects the outlet of steam generator 10 to the bottle supporting seat 15. Seat 15 has an opening 16 along the ring to discharge steam into the dispenser water reservoir 30. It should be appreciated that steam conducting pipe 17 can also be connected directly to the dispenser water reservoir without going through the bottle supporting seat.

Figure 5:
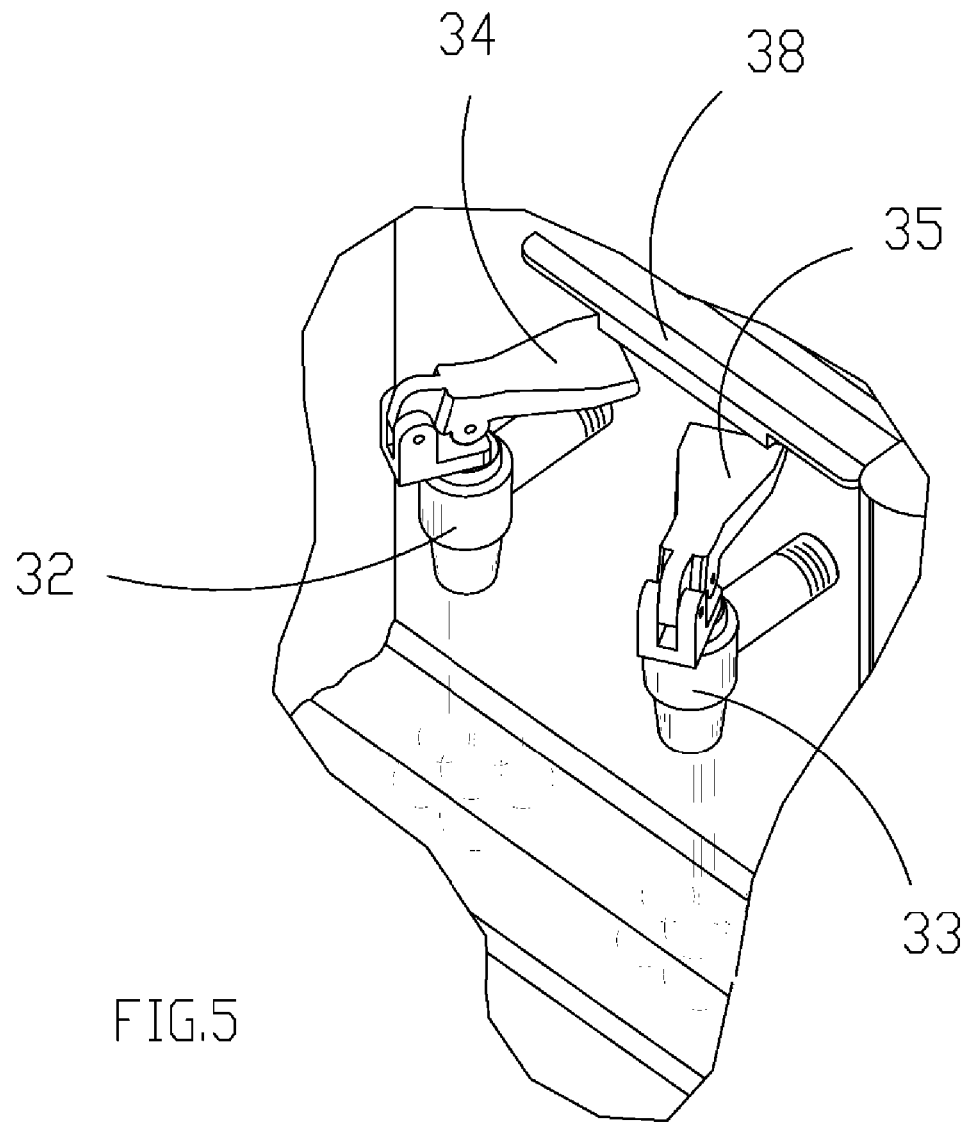
FIG. 5 is a perspective view of two taps and their handles locked by a stepped, protruded boss.

FIG. 5 shows a stepped mechanical boss 38 that can keep both taps 32 and 33 open during the steam cleaning period by locking down their handles 34 and 35 to allow for steam discharge. The step in the boss is to allow for adjustable aperture size for the taps where the steam discharges. The mechanical boss 38 can also provide additional convenience for a user who does not want to hold down the handle 34 and/or 35 while filling water to a cup.

Figure 6:
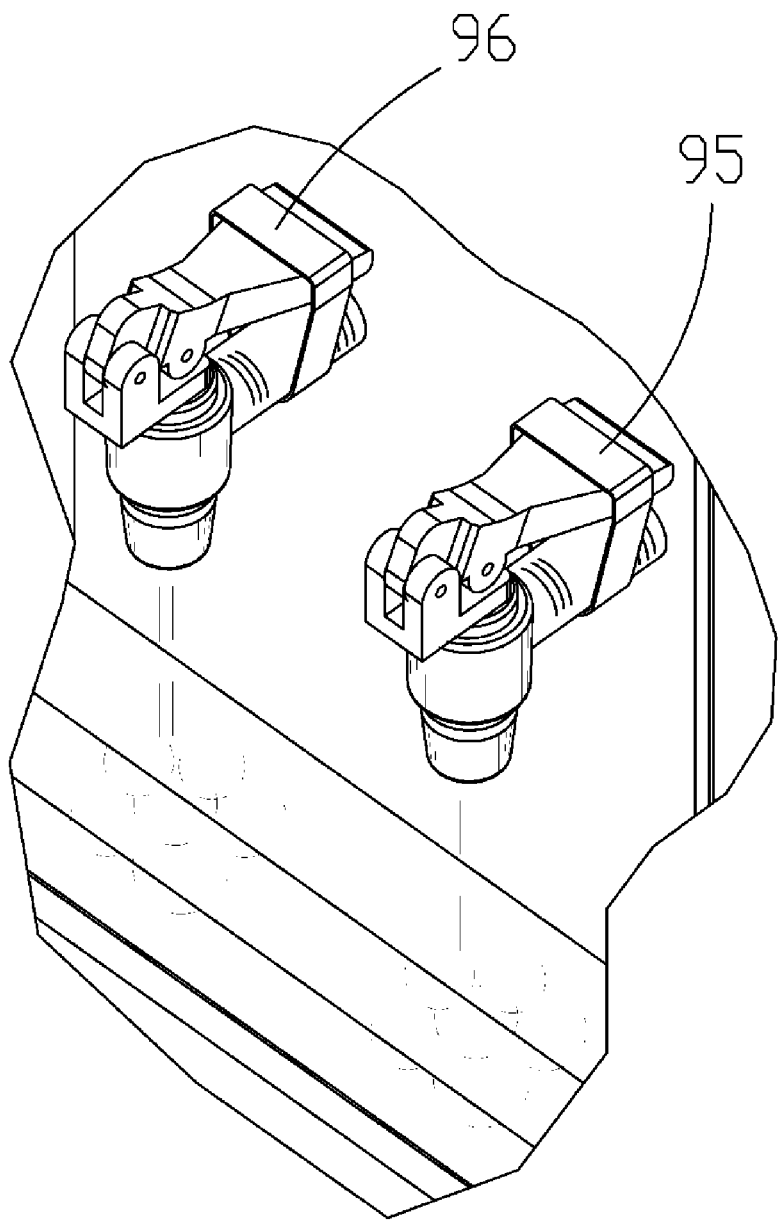
FIG. 6 is a perspective view of two taps with their handles held down by Velcro belts.

FIG. 6 presents a different way of holding the taps open using two Velcro belts 95 and 96.

What is claimed is:

1. An apparatus for disinfecting a water dispensing machine; the apparatus comprising:
   a bottle type water dispenser having a body an interior and a top having a bottle supporting seat;
   a reservoir contained within said body generally open at the said top for receiving water;
   the said reservoir in fluid communication by using a flow path with one or more taps for dispensing water; a water source that replenishes said reservoir;
   a steam generator physically integrated with said water dispenser;
   a water container to supply water to said steam generator;
   a flow control device to control water flow from said water container to a boiler for boiling water to produce steam;
   a steam outlet to output said steam.

2. An apparatus as defined in claim 1 has a removable cover substantially matching the said bottle supporting seat of said water dispenser to prevent hot steam from escaping at the said top of said water dispenser while performing steam disinfection.

3. An apparatus as defined in claim 1 can also use a capped water bottle to prevent hot steam from escaping at the said top of said water dispenser while performing steam disinfection.

4. An apparatus as defined in claim 1 uses an opening at said bottle supporting seat to inject steam into the said flow path of said water dispenser.

5. An apparatus as defined in claim 1 uses at least one said tap as a steam discharge port.

6. An apparatus as defined in claim 1 further comprising a boss to hold said tap at its open position to discharge said steam while disinfecting said water dispenser.

7. An apparatus of claim 6, wherein said boss can include steps for selectively controlling the orifice of said tap.

8. An apparatus of claim 1, wherein said water container is removable and has a cap for refilling water.

9. An apparatus of claim 2, wherein said removable cover has at least one pressure relief valve for preventing excessive pressure inside said water dispenser during disinfection period.

10. An apparatus of claim 1 can use loop fastener as an alternative way of holding said tap at its open position to discharge the steam.

11. The steam generator of claim 1, wherein said flow control device is a pump, electronic valve or a combination of said pump and said electric valve that controls water supply to said boiler and isolates said water container from the boiler.

12. An apparatus of claim 1, further comprising a thermostatic control for controlling a temperature range at which said steam is generated.

13. An apparatus of claim 1, further comprising a timer to control the period of steam generation.

\* \* \* \* \*